United States Patent
Strehlau et al.

(10) Patent No.: US 6,862,533 B2
(45) Date of Patent: Mar. 1, 2005

(54) COMPUTER-AIDED OPTIMIZATION OF SUBSTANCE LIBRARIES

(75) Inventors: Wolfgang Strehlau, Dossenheim (DE); John Michael Newsam, San Diego, CA (US); Dirk Demuth, NuBloch (DE); Wolfram Stichert, Heidelberg (DE); Armin Brenner, Eppelheim (DE); Stephan A. Schunk, Heidelberg (DE); Jens Klein, Heidelberg (DE)

(73) Assignee: hte Aktiengesellschaft the high throughput experimentation company, Heidelberg (DE)

( * ) Notice: Subject to any disclaimer, the term of this patent is extended or adjusted under 35 U.S.C. 154(b) by 523 days.

(21) Appl. No.: 09/876,142

(22) Filed: Jun. 8, 2001

(65) Prior Publication Data

US 2003/0203400 A1 Oct. 30, 2003

(30) Foreign Application Priority Data

Jun. 10, 2000 (DE) .......................... 100 28 875

(51) Int. Cl.[7] ............................................. G01N 31/00
(52) U.S. Cl. .............................. 702/22; 702/30; 702/31
(58) Field of Search ..................................... 702/22–32

(56) References Cited

U.S. PATENT DOCUMENTS

| | | | |
|---|---|---|---|
| 5,463,564 A | | 10/1995 | Agrafiotis et al. .......... 364/496 |
| 5,880,972 A | * | 3/1999 | Horlbeck ..................... 702/27 |
| 5,901,069 A | | 5/1999 | Agrafiotis et al. ..... 364/528.03 |
| 5,961,923 A | * | 10/1999 | Nova et al. ................. 422/68.1 |
| 6,269,312 B1 | * | 7/2001 | Mayo et al. ................. 702/19 |
| 6,500,609 B1 | * | 12/2002 | Ribeill et al. .................. 435/4 |
| 6,535,824 B1 | * | 3/2003 | Mansky et al. ............... 702/30 |
| 6,625,546 B2 | * | 9/2003 | Sepetov et al. ............... 702/19 |
| 2002/0049548 A1 | * | 4/2002 | Bunin ......................... 702/32 |

FOREIGN PATENT DOCUMENTS

| | | | | |
|---|---|---|---|---|
| WO | WO 92/01933 | * | 2/1992 | .......... G01N/33/00 |
| WO | 99/41005 | | 8/1999 | |
| WO | 00/23921 | | 4/2000 | |

OTHER PUBLICATIONS

Danieison et al. A Combinatorial Approach to the Discovery and Optimization of Luminescent Materials, Letters to Nature, vol. 389, Oct. 30, 1997, pp. 944–948.

* cited by examiner

Primary Examiner—Marc S. Huff
Assistant Examiner—Anthony Gutierrez
(74) Attorney, Agent, or Firm—Jones Day

(57) ABSTRACT

The invention relates to a method for the automated production and iterative automated optimization of a substance library and/or at least one reaction parameter relating to a performance characteristic comprising at least two substances comprising the steps of: a) defining at least one production parameter and at least one test parameter; b) automated preparation of a substance library by producing at least two substances on the basis of the at least one production parameter; c) automated testing of the at least two substances of the substance library with respect to at least one performance characteristic on the basis of the at least one test parameter; d) evaluating the test using electronic data analysis; e) varying the at least one production parameter and/or the at least one test parameter for optimizing the performance characteristics, and single or repeated repetition of steps b) to e) or c) to e); characterized in that the steps b) to e) are carried out in an integrated automated process.

32 Claims, 9 Drawing Sheets

COMPUTER-AIDED OPTIMIZATION OF SUBSTANCE LIBRARIES

BACKGROUND OF THE INVENTION

1) Field of the Invention

The present invention relates to an apparatus and a method for optimizing substance libraries comprising at least two substances.

More precisely, the invention relates to a computer-aided method which permits the successive material optimization of non-molecular substance libraries with respect to a defined application and/or the optimization of the test parameters which are relevant to the application or are important to the process of selected substances within a predefined parameter space or a parameter space resulting during the optimization (altered with respect to the predefined parameter space), an apparatus suitable therefor, comprising a substrate, the substance library per se which can be produced in this way and a computer program for controlling the inventive method.

In the context of the inventive method it is possible to optimize substance libraries comprising molecular and non-molecular substances.

2) Description of Related Art

The preparation of substance libraries in pharmaceutical combinatorial research generally begins with designing a hypothesis regarding the interaction of an active compound molecule (for example a ligand) with a biological target (receptor). The type and strength of interaction here are associated with discrete structural properties of the active compound molecule (SAR—structure activity relationship). The term "structural property" includes here, for example, topology, conformation, spatial arrangement of substituents or electronic configuration of the active compound molecules. These "structural properties" are incorporated as descriptors, that is to say as parameters for describing the interaction(s) between active compound molecule and receptor. The classical combinatorial approach is based on the systematic change (permutation) of the structural properties of one or more (molecular) organic base skeletons. This presupposes the existence of suitable organic building blocks (for example a methyl or phenyl group) which react under defined synthesis conditions with the base skeleton to form a target molecule of the planned substance library. After determining the activity of the molecules synthesized within the substance library against a biological target, the hypothesis originally made is revised with the objective of producing an optimized substance library.

U.S. Pat. Nos. 5,901,069 and 5,463,564 disclose systems and methods for the at least partial automated generation of (chemical) compounds having desired chemical or bioactive properties.

There, starting from an initial hypothesis relating to the interactions of interest and the structural features required for this, a computer-aided process is carried out which during each iteration comprises the following steps:

(1) a library consisting of a plurality of compounds is robotically generated in accordance with robotic system instructions;

(2) the compounds in the library are analysed in order to identify those compounds which have the desired useful properties;

(3) structure-activity data are utilized in order to select compounds which are to be synthesized in the next iteration; and (4) new robotic system instructions are generated by the experimenter which control the synthesis of the compounds in the library for the next iteration.

As an aid to refining the hypothesis initially made in pharmaceutical research, suitable software is available for modeling and visualizing molecules, or else mathematical/statistical software which comprises, for example, regression methods, for example linear single or multiple regression, for quantifying the structure-activity relationship (QSAR—quantitative structure activity relationships). In the literature, corresponding computer-aided methods for pharmaceutical applications are also termed CADD (computer-aided drug design) or CAMD (computer-aided molecular design).

The systems and methods disclosed in these publications are not fully automated for optimization, that is to say the experimenter must intervene at one or more time points when the method is being carried out. In addition, the change(s) made to the "structural property" in these methods is (are) always carried out by varying discrete states, that is to say for example dependent on the variation of a substitution pattern, for example methyl→ethyl→propyl→ . . .

In summary, the above described implies that the targeted optimization, which is not based exclusively on trial and error, of molecular organic libraries is based on the following principles:

a) assuming a relationship between structure and activity of a molecule in question (SAR);

b) existence of suitable synthetic building blocks;

c) variation of discrete molecular properties;

d) use of molecular descriptors.

Whereas points a) and d) do not represent a fundamental precondition for the combinatorial variation of an organic base skeleton, points b) and c) are an essential necessity therefor.

Since in the case of non-molecular substances the required relationships between structure and activity of the substances are often unknown, and corresponding molecular descriptors do not exist, for the complete integration of the generation of non-molecular substance libraries, recourse cannot be made to the methods for library optimization in pharmaceutical active compound research.

The preparation and testing of non-molecular substance libraries outside pharmaceutical research is described in a range of publications. In this sector, production, testing and evaluation of the substance libraries are represented as separate process steps. However, the complete integration of the individual process steps in to a joint software environment has not yet been described to date, as can be seen from the following summary of the relevant prior art:

Danielson et al. describe a combinatorial method for discovering and optimizing luminescent substances (Nature, vol. 389, p. 944, 1997). The method of Danielson comprises the automated production of a first substance library, testing the first substance library in order to identify lead materials, and designing and synthesizing newly optimized substance libraries by the experimenter on the basis of the composition of the lead substances identified. According to Danielson, the combinatorial exploration requires different iterations in order to optimize the composition and production for a defined application. The iterative optimization according to Danielson is based, however, solely on the intuition of the experimenter without the use of computers or the use of software-controlled optimization methods.

WO 00/23921 relates to a computer-controlled method for generating a library design for a combinatorial material library which comprises:

defining one or more sources and one or more destinations, each source being an electronic data point representing a component for preparing the combinatorial library and each destination being an electronic data point representing an arrangement of cells;

receiving an input which defines the first mapping, this first mapping being electronic data defining a distribution pattern for assigning a component to cells in the arrangement, the distribution pattern defining a minimum and a maximum amount of the component and a gradient between the minimum and the maximum amounts of the component across the multiplicity of the cells;

using the first mapping to calculate a composition of one or more materials to be assigned to one or more of the cells; and generating a data file for defining the library design, the data file comprising electronic data representing the sources, the destinations and the mapping.

According to this publication, therefore, only the automated production of material libraries is described or claimed.

SUMMARY OF THE INVENTION

One object of the present invention is to provide an integrated system and method for producing and optimizing non-molecular substance libraries which makes it possible to optimize a substance library without intervention, or with only marginal intervention, for example in the form of a plausibility analysis of an operator.

This object and other objects are achieved according to the invention by a method for the automated production and iterative automated optimization of a substance library and/or at least one reaction parameter comprising at least two substances comprising the steps:

a) defining at least one production parameter and at least one test parameter;

b) automated preparation of a substance library by producing at least two substances on the basis of the at least one production parameter;

c) automated testing of the at least two substances of the substance library with respect to at least one wanted useful property on the basis of the at least one test parameter;

d) evaluating the test using electronic data analysis;

e) varying the at least one production parameter and/or the at least one test parameter for optimizing the wanted useful properties, and single or repeated repetition of steps b) to e) or c) to e);

wherein the steps b) to e) are carried out in an integrated automated process and by an apparatus for the automated production and iterative automated optimization of a substance library, comprising:

a) means for defining at least one initial production parameter and at least one test parameter;

b) an arrangement for the automated production of the at least two substances of a substance library on the basis of the at least one production parameter;

c) a test device for the automated testing of the at least two substances of the substance library with respect to at least one performance characteristic on the basis of the at least one test parameter;

d) a data analysis system for evaluating the test;

e) device for varying the at least one production parameter and/or test parameter for optimizing the performance characteristics, characterized in that f) the apparatus in addition comprises means for the integrated and iterative automated control of steps b) to e) or c) to e).

Further objects, features and advantages of the present invention, will become readily apparent from detailed consideration of the preferred embodiments which follow.

DETAILED DESCRIPTION OF THE PREFERRED EMBODIMENTS

Figure 1:
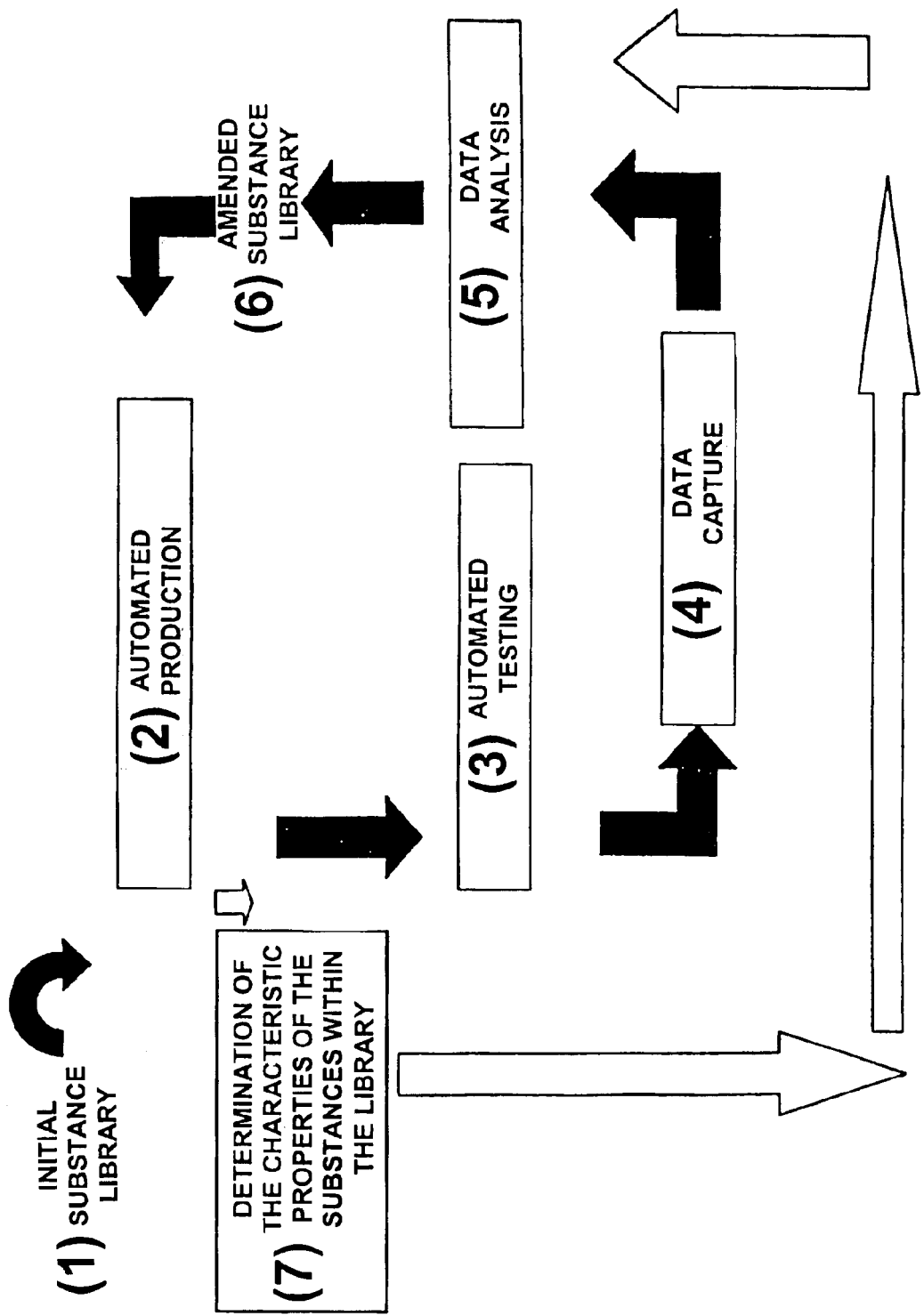
FIG. 1 shows a flow diagram of an embodiment of the inventive method.

The basis for the inventive method and the inventive apparatus is the correlation of sets of at least one production parameter and/or test parameter ("experimental descriptors") and optionally characteristic properties ("first or second order characteristics") of the substances of the substance libraries with their performance characteristics within a method integrated with respect to control software, data capture software and data evaluation software and a corresponding apparatus.

The optimization of the non-molecular substance libraries and/or reaction conditions is carried out in an interative process in which an initially given non-molecular substance library which is characterized by production properties and thus characteristic properties, comprising at least two substances, is initially subjected to one or a multiplicity of precise defined tests of defined performance characteristics. By applying mathematical algorithms, the significance of the individual parameters in the production and/or test parameter sets and/or characteristic properties to the test result is tested, the appropriate parameter space is constricted or changed and optimized parameter sets are prepared. The optimized (generally changed with respect to the predefined parameter sets) parameter sets then form the basis for the preparation of the production parameter or production parameters for the substances of the next substance library and/or for establishing new test parameters. To obtain such optimized parameter sets, information from one or more libraries can be used or else evolutionary algorithms and other mathematical or statistical methods can be used.

In addition, in the context of the inventive method, not only different substance libraries can be studied and optimized under the same test conditions, but the same substance libraries can be studied and optimized under different test conditions.

Furthermore, the interaction between the (chemical) constitution of the substances within the optimized substance libraries and the possible variation of the test parameters, there also results the possibility of simultaneous optimization of the substances of the material library with respect to their performance characteristics and test conditions which typically relate to the optimization of at least one reaction parameter with respect to later use of one or more substances within the substance library, in which case here likewise the work can be carried out in such a manner that not only are the substances within the substance library and the at least one reaction parameter optimized simultaneously, but, with respect to a defined, typically previously optimized, substance library, further attempts are made to optimize the reaction parameters.

The iterations can be repeated until either the explorative destination is reached or the optima within one or more preset parameter space or parameter spaces are reached. The efficiency of the inventive method COALA (Computation Assisted Library Amendment) results from the integration of the production parameters and test parameters and of the characteristic properties and test data in a shared software environment preferably under real time conditions.

It is a further advantage of the inventive method that this can be used for an optimization over short and also long periods, that is to say either a substance library is optimized (short period) or optimization is performed over the total of a plurality of substance libraries (long period). A parameter set for an improved library is always obtained after processing of a substance library.

A diagrammatic description of one embodiment of the inventive method is given in FIG. 1. In the figure (1) designates an initial substance library, (2) designates the automated production, (3) designates the automated testing, (4) designates data capture, (5) designates data analysis, (6) designates amended substance library and (7) designates determination of the characteristic properties of the substances within the substance library.

The terms used in the context of the present application may be clarified at this point:

Substance library: The term "substance library" designates an arrangement comprising at least two, preferably up to 10, further preferably up to 100, in particular up to 1000, and further preferably up to 100,000 substances, or (chemical) compounds, mixtures of (chemical) compounds, materials, formulations which are present in the solid, liquid or gaseous state on/in a substrate.

Preferably, in the context of the present invention, substances of the above meaning are non-gaseous substances, for example solids, liquids, sols, gels, waxy substances or substance mixtures, dispersions, emulsions, suspensions and solids, particularly preferably solids. In the context of the substances used according to the invention, the substances can be molecular and non-molecular chemical compounds or formulations or mixtures or materials, the term "non-molecular" defining substances which can be continuously optimized or amended, in contrast to "molecular" substances whose structural property may only be changed by varying discrete states, that is to say for example varying a substitution pattern.

The substances in the substance library can be identical or different from one another, the latter being preferred; however, in an optimization of test parameters or reaction parameters or process parameters, it is also easily possible that the substance library comprises two or more identical substances or consists exclusively of identical substances.

Virtual substance library: This is a substance library which has been designed by or using a computer and in which it still remains to be tested, for example by an operator or computer, as to whether the substances or substance classes within the substance library can actually be prepared. In the context of a virtual library, on the basis of available information with respect to the requirements of a substance when used in a defined chemical, physicochemical or physical reaction, for example, a substance library can be one consisting of substances which have been "freely" generated by the computer on the basis of these data.

Initial substance library: The substance library designed at the beginning of the inventive method for optimization; this can correspond to the virtual substance library, can be modified in comparison with this or be designed by an operator without including the preparation of a virtual substance library.

Amended substance library: Substance library improved by establishing new production and/or test parameters which is then subjected to an inventive iteration (optimization).

Substance: Unit situated in the respective substrate sections within the substance library, and which can consist of one or more components.

Substrate: Device having a rigid or semi-rigid surface which can be either flat or also have recesses or bore holes or channels. The substrate must be suitable for separating the at least two substances physically from one another in the at least two different sections separated from one another. The substances can be arranged one-dimensionally, two-dimensionally or three-dimensionally in the substrate, that is to say next to one another and one above the other in different planes.

Preferably, the substrate comprises parallel continuous channels and can have, inter alia, a wire grid or a foamed ceramic.

Further preferably, the substrate is a tube-bundle reactor, in particular a tube-bundle reactor as described in WO 99/41005 and its disclosure in this respect is incorporated by reference in its entirety into the context of the present application.

Performance characteristics: These are measurable characteristics of the substances of the substance library which can be determined within an automated testing and which are optimized in the context of the inventive method: examples of these are mentioned in the further course of the description.

Automated production: Preparation of the substance library and of the substances of the substance library using substantially automated preparation modules which are incorporated in a suitable control software.

Automated optimization: Carrying out one or more automated optimization steps.

Test parameters: One or more changeable variables which establish the type and conditions of the automated testing.

Reaction parameters: Special case of the test parameter which, if it is in the case of the test the performance of the substance library in the context of a defined (chemical) reaction, establishes the type and conditions of this reaction.

Analysis parameters: Further subgroup of the test parameters which establishes the type and conditions in the determination of the characteristic properties of the substances within the substance library.

Parameter space: Totality of all parameters which describe the production and/or testing of the substance library within the context of individual steps or the totality of the inventive method, with in this case only preferably the strictly mathematical or scalar definition of a collection of non-redundant vectors being used for the description of the test parameters and/or reaction parameters and/or production parameters, that is to say the parameter space can also comprise redundant vectors or scalars.

Output parameters: Analogue or analogue to digital converted data from the production, test and characterization instruments to the file server.

Analysis: Term which comprises all of the analytical methods for testing substances within a substance library for determining their characteristic properties.

Characteristic properties: This term represents the structural features or the description of the structural features of a non-molecular material by employing physicochemical methods. "First order characteristics" are very largely those characteristic properties which are obtained using physical characterization methods, for example X-ray diffraction, LEED structure determination, EDX, X-ray fluorescence analysis; X-ray photoelectron spectroscopy, auger spectroscopy.

"Second order characteristic" is taken to mean those characteristic properties which are accessible using physicochemical characterization methods, for example nitrogen adsorption—(surface dimensions, (BET)); TPD—(bonding strengths of adsorbates to surfaces or selective chemisorption—size of the surfaces of active centres).

Automated testing: Collective term for tests of one or more performance characteristics which proceed automatically. Automated testing is completely integrated into the software.

Data acquisition: Capture of all parameters (production or test parameters), characteristic properties and test results.

Test results: Data sets such as production and/or test parameters, characteristic properties and performance characteristics, in particular with respect to the characteristics to be optimized.

Data analysis: Computer-aided data evaluation using various mathematical/statistical or evolutionary algorithms.

Sensitivity analysis: Mathematical method for differentiating statistically significant factors from non-significant factors within linear or non-linear equation systems.

Virtual screening: Optimization of substance libraries using data processing systems using databases and modeling by means of software-supported analytical methods.

Modified production parameters and/or test parameters:

Production parameters and/or test parameters which have been modified in comparison with the initial production parameters and/or test parameters and have generally been optimized, for example with process optimization as a target.

Software: Software which comprises the components for process control, data transfer, data formatting, data storage, data search, data management and for data interpretation and data evolution and is preferably operated under real-time conditions.

Input parameters: Digital or digital to analogue converted data from the control computer/process control system for controlling the production, test and characterization instruments (information).

Output information: Digital or digital to analogue converted data which corresponds to the results of the testing of the substance library in the respective optimization step.

Optimization step: Sequence of production and testing the substance library including analysis of the test results which is incorporated in a suitable control and evaluation software.

Production module: Totality (arrangement) for the automated production of the substances within the substance library.

Test module: Device or arrangement for the automated testing of the performance characteristics of the substances and/or optimization of one or more reaction parameters.

System time/date: The time coordinate which is preset by the data processing system and makes possible unambiguous alphanumeric assignment of all processes occurring during the method.

System location: Location which is unambiguously defined within the totality of the arrangement for production, testing and analysis of the substances.

The present invention enables a) the information (input parameter and output information) which is obtained in the process steps shown in FIG. 1 (i.e. automated synthesis, analysis and automated testing) to be integrated in a collective software environment and b) in the sense of a self-optimizing method, using mathematical algorithms on the output data, to arrive at a successive improvement in the production parameters and/or test parameters of the subsequent (=optimized) non-molecular substance libraries. In principle the inventive method also offers the possibility of using the characteristic properties of the substances of the substance library ("$1^{st}$ and $2^{nd}$ order") as a basis for the optimization of the substance library. The latter embodiment is difficult to achieve especially in the area of heterogeneous catalysis:

a) Characteristic properties of non-molecular catalysts are always to be taken as an average over a virtually infinitely large structure and do not characterize the individual active centre of an atomic level. Since the totality of the active centres determines the activity and selectivity of a catalyst, an average, in contrast, may not be usable for the desired correlation.

b) It is always questionable whether all of the characteristic properties which determine the activity and selectivity of a catalyst can be determined. In every case, the time consumed to carry out corresponding measurements and for modelling based on this would be considerable.

c) If the knowledge of the optimum qualities of the active centres were actually available, it would nevertheless be questionable as to whether a corresponding material could actually be synthesized by suitable choice of the production parameters.

d) The characteristic properties of a material can differ greatly from one another during the analysis and testing owing to shaping and conditioning processes.

For these reasons, in the present invention, it is not primarily the characteristic properties ("first and second order characteristics") which are used as a basis for library optimization but preferably the production parameters ("experimental descriptors"), since these, regardless of the structural qualities of the substances, permit correlation with the performance characteristics. Procedures as used in pharmaceutical active compound research for optimizing molecular structures, that is to say based on the characteristic parameters ("first and second order characteristics"), can, for the reasons a) to c) given above, only be used in exceptional cases for optimizing non-molecular substances or formulations or materials. Examples within non-molecular material research in which the characteristic properties ("first and second order characteristics") can at least partially be correlated with the performance characteristics are:

a) zeolites: acidity and pore diameter correlate with cracking activity and/or isomerization activity and selectivity;

b) structure-insensitive reactions: Fischer-Tropsch activity and selectivity is frequently correlated with the size of the material particle situated on the catalyst surface;

c) semiconductors: UV-spectra provide conclusions with respect to electronic transitions;

d) pigments: layer thicknesses can correlate with the colour.

Figure 2:
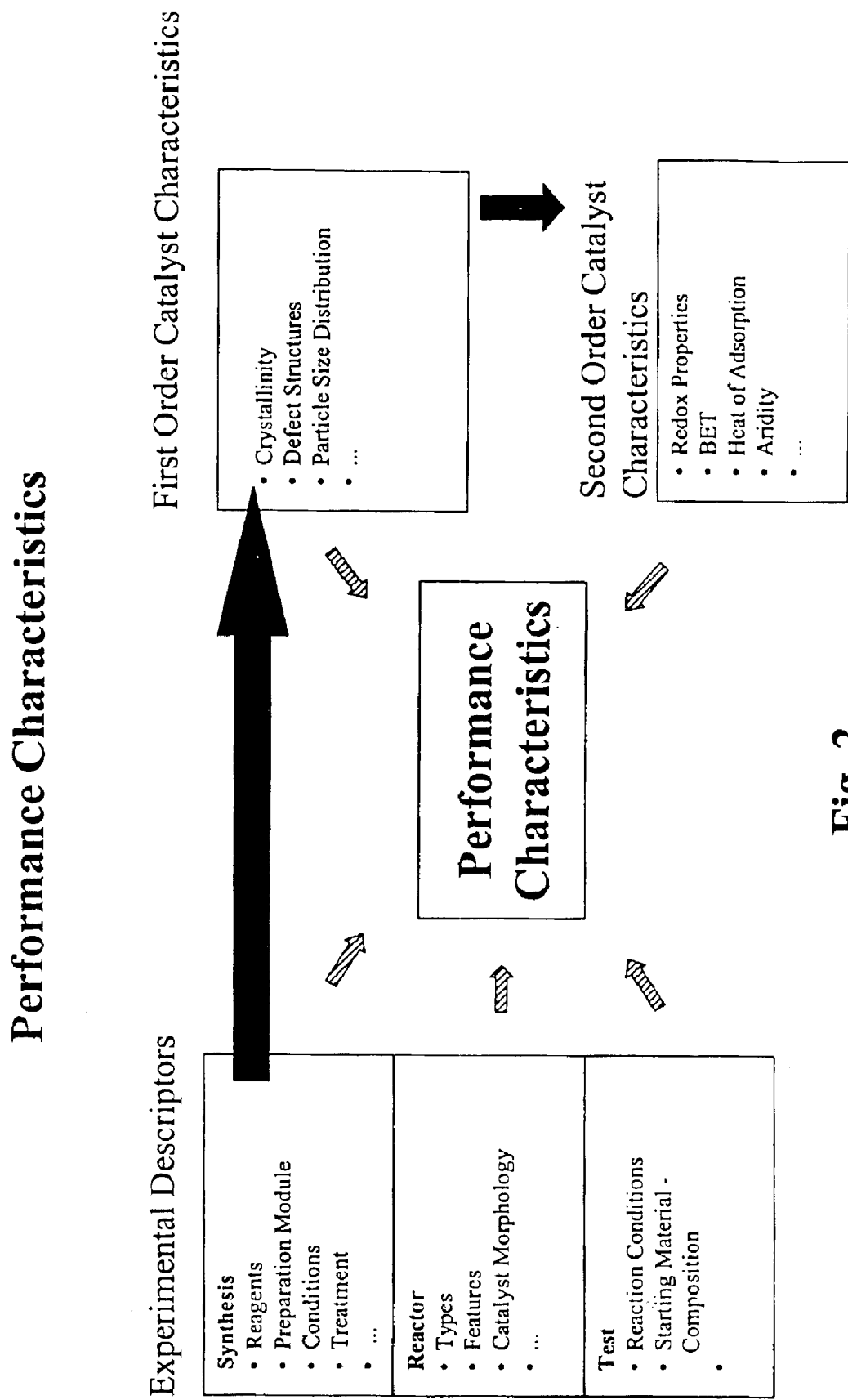
FIG. 2 shows the relationship between production parameters and test parameters and the performance characteristics of a catalyst.

Examples a) to d) represent only a very small section within the bandwidth of non-molecular substances. The relationship between production parameters and test parameters and characteristic properties and the performance characteristics of a catalyst is shown in FIG. 2.

As can be seen from this figure, initially the synthesis (production parameters) is directly responsible for the first order catalyst characteristics, for example crystallinity, defect structure or particle size distribution. These first order catalyst characteristics then in turn determine the second order catalyst characteristics, for example redox characteristics, BET surface area, heat of adsorption or acidity. Both the first order catalyst characteristics and the second order catalyst characteristics then determine the performance characteristics which obviously in turn depend on the other experimental descriptors, that is to say the reaction parameters, for example reactor and the test parameters, for example reaction conditions and starting material composition.

Figure 3:
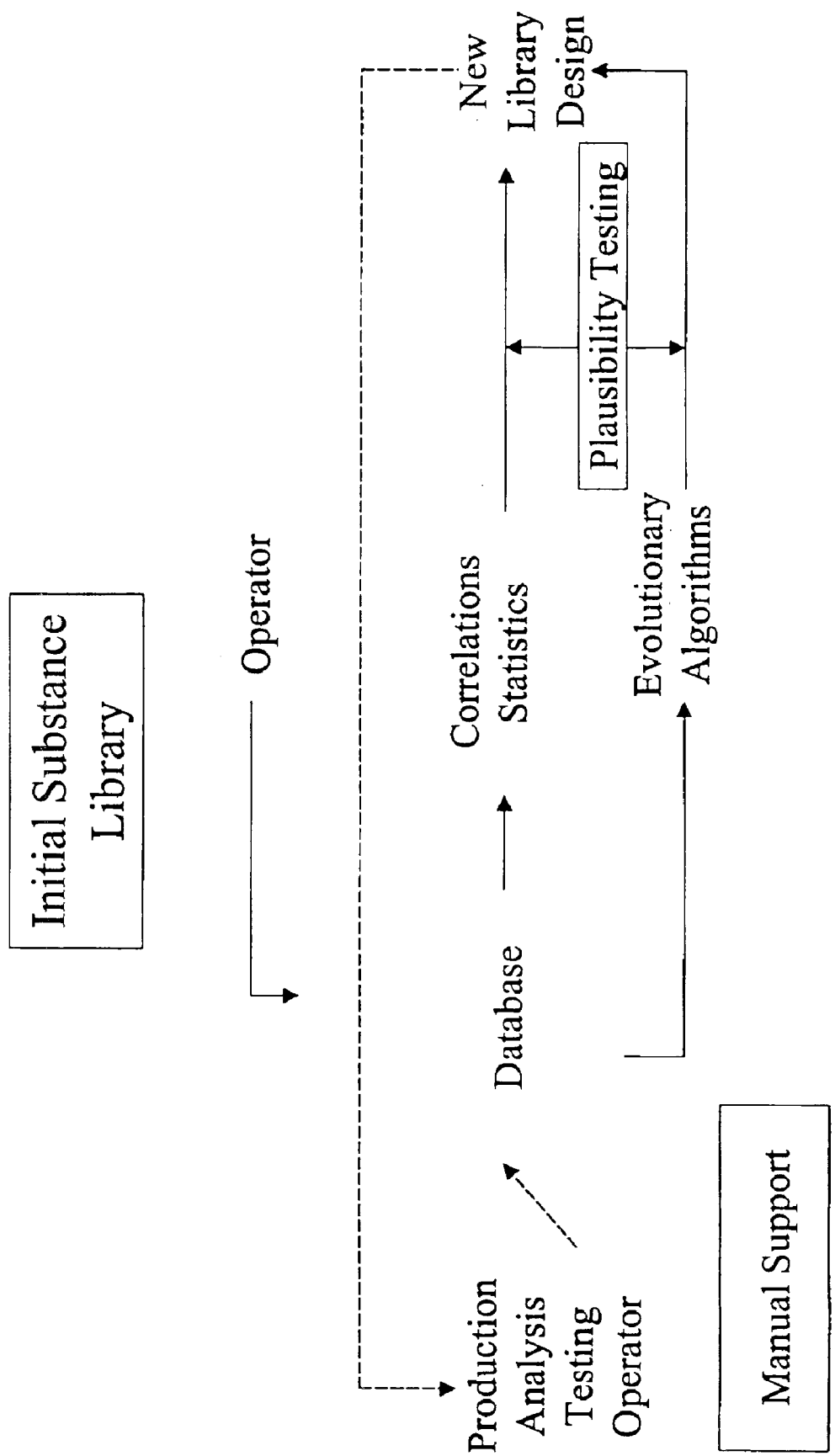
FIG. 3 summarizes diagrammatically the possible interventions by an operator of the inventive apparatus.

The present invention indicates a route which permits 1. logical links to be made between the production parameters and/or if appropriate also characteristic properties of substances of non-molecular, non-trivial substance libraries and their performance characteristics;

2. logical links to be made between the test parameters of substances of non-molecular, non-trivial substance libraries in a multidimensional test parameter space and the performance characteristics of these substances, where the software environment, with only a small amount of intervention by the user is able to repeat the process steps production, testing and if appropriate analysis each time with an improved or mutated set of production parameters or test parameters until the optimum of a material or the optimum of the test conditions has been experimentally found or can be mathematically predicted. The role of the operator (FIG. 3) is essentially restricted to defining chemically useful initial libraries, to operating manually diverse production modules whose full automation is technically difficult or is currently impossible to achieve, and to testing the results of the computer-aided data evaluation for plausibility. With advancing automation, it is absolutely conceivable to carry out the inventive method in a fully automated manner, that is to say the operator inputs the desired performance characteristics and test parameters, while the inventive method carries out optimization of the substance library starting from a virtual substance library. The operator then receives the results of the data analysis and can thus obtain the optimized substance and the optimum reaction conditions and can then immediately implement this knowledge, for example, on a laboratory or pilot-plant scale. Although this fully automated procedure is already possible even now, it fails in many cases due to the fact that the data required to prepare a virtual substance library are not available or are insufficient and knowledge on the relationship between characteristic properties and performance characteristics is insufficient or unavailable.

Figure 4:
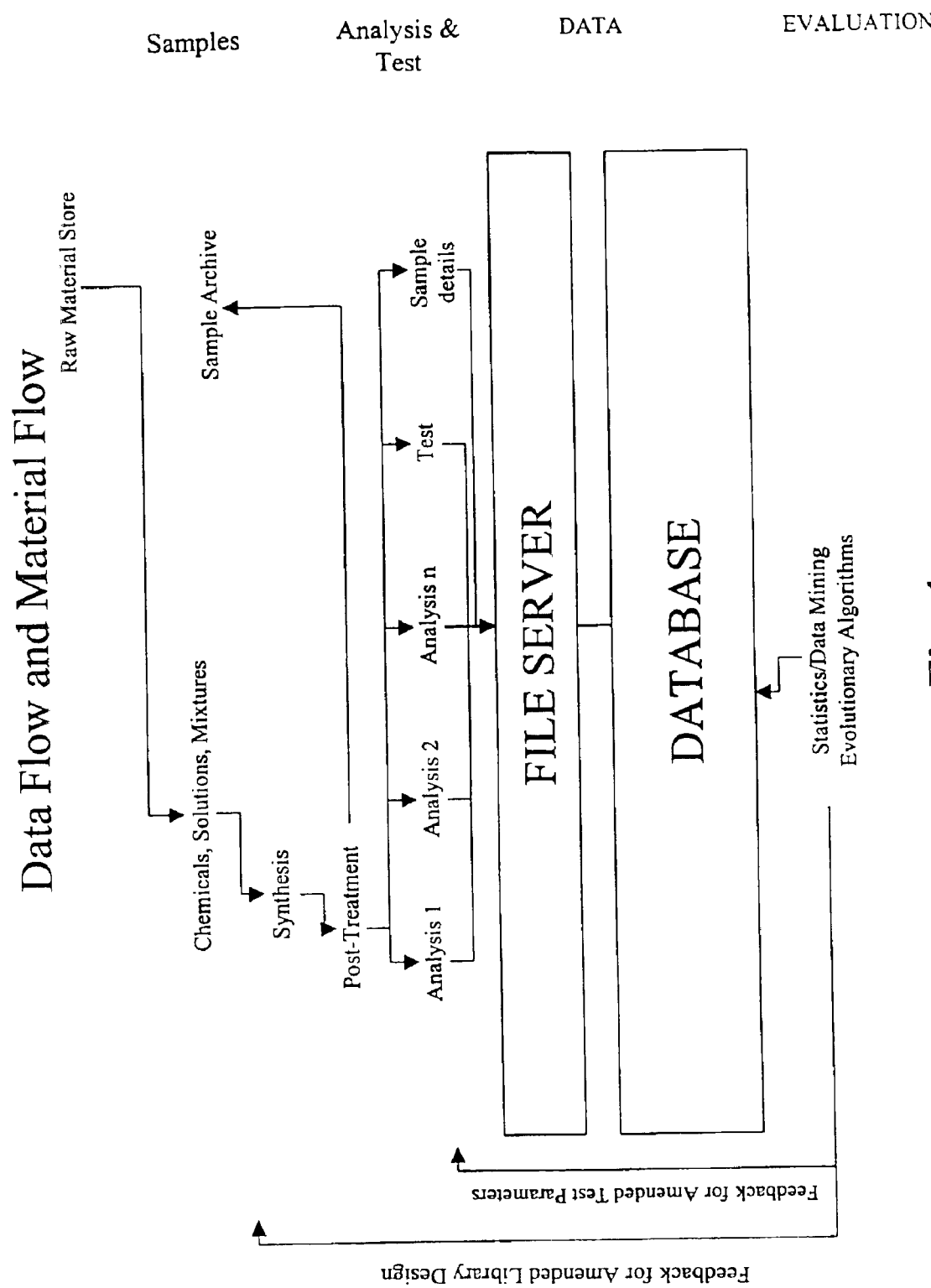
FIG. 4 shows the data flow and material flow when the inventive method is carried out.

Preferably, as shown in FIG. 4, the characteristic properties are captured in parallel to the production parameters and test parameters and deposited in a shared database. By chemical plausibility testing, then, if appropriate, the suitability of characteristic properties for optimizing non-molecular libraries must be decided on a case-by-case basis.

The methodology illustrated in FIGS. 1 and 4 may be described as follows:

Definition of the Initial Substance Library:

This requires establishment of the production parameters by which the production of the substances within the substance library is unambiguously describable. The production parameters of the initial library can differ greatly, for example on a logical basis, that is to say based on parameters taken from the literature, on production parameters considered expedient chemically or else on the basis of mathematically determinable production parameters for non-molecular substances and are shown by way of example in Table 1 for three different production methods (that is to say 1. precipitation, 2. metal adsorption and 3. incipient wetness). Each individual production parameter can affect the characteristic properties and thus indirectly also the performance characteristics of the substance. Apart from a few exceptions, for example the type of precursor or support material, every other production parameter can be varied semicontinuously. Here there is a marked difference to the optimization of organic molecules discussed at the outset which is based on the variation of discrete molecular structures.

The substances within a substance library used according to the invention are not restricted in a particular manner. The substances can be molecular, non-molecular or else formulations and materials. Those which may be preferably mentioned are the following classes of such substances:

heterogeneous or heterogenized catalysts, luminophores, electrooptical, superconducting or magnetic substances, or mixtures of two or more thereof; in particular intermetallic compounds, oxides, oxide mixtures, mixed oxides, ionic or covalent compounds of metals and/or non-metals, metal alloys, ceramics, organometallic compounds and composite materials, dielectrics, thermoelectrics, magnetoresistive and magnetooptic materials, organic compounds, enzymes, active pharmaceutical compounds, substances for foodstuffs and food supplements, feedstuffs and feed supplements and cosmetics.

The substances here can be identical or different from one another that is to say with reference to the (chemical) components per se which make up the material, or else in the concentration of identical components in a material to be investigated.

Automated Production

The control program of the individual synthesis modules determines directly the establishment of the production parameters. Module in this context is taken to mean a synthesis unit which is independent in principle, for example a liquid or solids metering unit or a filtration and washing unit. In the case of optimum system integration, the modules are controlled by a shared computer-aided control program or process control system and the individual sequences of the modules are controlled by suitable interaction of the sensors and actuators. The control system preferably causes a synchronization of sensors and actuators on a real-time basis. The production parameters and the definition or characteristics of the synthesis modules used are preferably stored as information in a database and in parallel thereto are converted into physical data (DA conversion) for controlling the synthesis modules. The information path to the database is generally accomplished via AD conversion and subsequent formatting of the data sequences.

Analysis

The characteristic properties of the substances ("$1^{st}$ and $2^{nd}$ order properties") which can be obtained by various analytical methods, are also stored as information in the database. Depending on the analytical method used, the information is either of discrete or continuous nature. For example, the information as to whether a defined radiographic phase having particular performance characteristics is present or not is of discrete nature, whereas the report of the percentage content of this phase in the material is information of continuous or indiscreet nature.

Automated Testing

Automated testing initially requires definition of the test modules and establishing an initial set of the test parameters which unambiguously describes the test or the test sequence. Typical test parameters (for catalysts) comprise firstly test conditions such as concentration of the starting material stream, gas throughput/space velocity, temperature and pressure and secondly characteristic reactor data such as reactor type, heat conductance, dimensions and residence time characteristics, for example residence time and/or space velocity. In addition, depending on the type of substances in the substance library, electrical, thermal, mechanical, morphological, optical and magnetic test parameters can be determined, for example superconducting characteristics, critical current, critical magnetic field, conductivity, resistance, dielectric constants, strength and dielectric loss, polarization, piezoelectricity, expansion coefficient, thermal conductivity, vapour pressure; tension, anisotropy, adhesion, hardness, density, elasticity, porosity; crystallinity, microstructure, surface properties, crystal orientation; refractive index, absorption, birefringence, spectroscopic characteristics, emission, turbidity; magnetic resistance, coercivity, magnetic susceptibility; permeability, purity, complexing.

Ideally, the test parameters and the definition of the test modules are stored as information in a database and converted into physical data in parallel for controlling the test modules. In addition, there follows the simultaneous display and evaluation of the test results which are stored as information in the database. The test parameters and analytical data are generally of discrete (component/product present, yes or no) and continuous (concentration of the component) nature.

Data Capture

Data capture within the database provides that every substance of the substance library, in addition to a sample ID, is assigned all information from the automated synthesis, analysis and automated testing. For traceability, the information is preferably completed by specifying system time, system location and the data. The unambiguous assignment of a sample and a result is made via a time signature and a reading unit, for example a barcode reader. Linking the automated production and testing and the analysis to a shared software environment ensures data security and data integrity.

Data Analysis

Figure 5A:
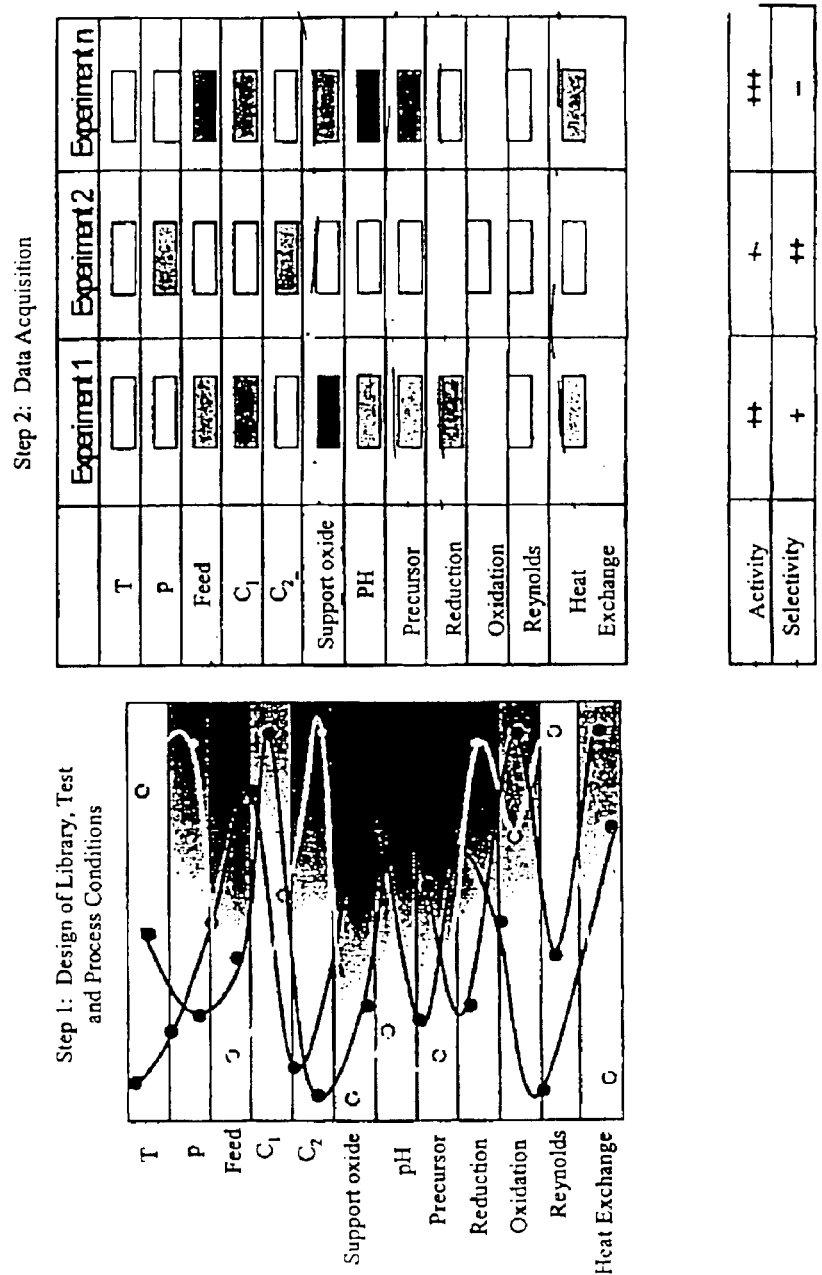
FIG. 5a shows the design and test of an initial substance library.
Figure 5B:
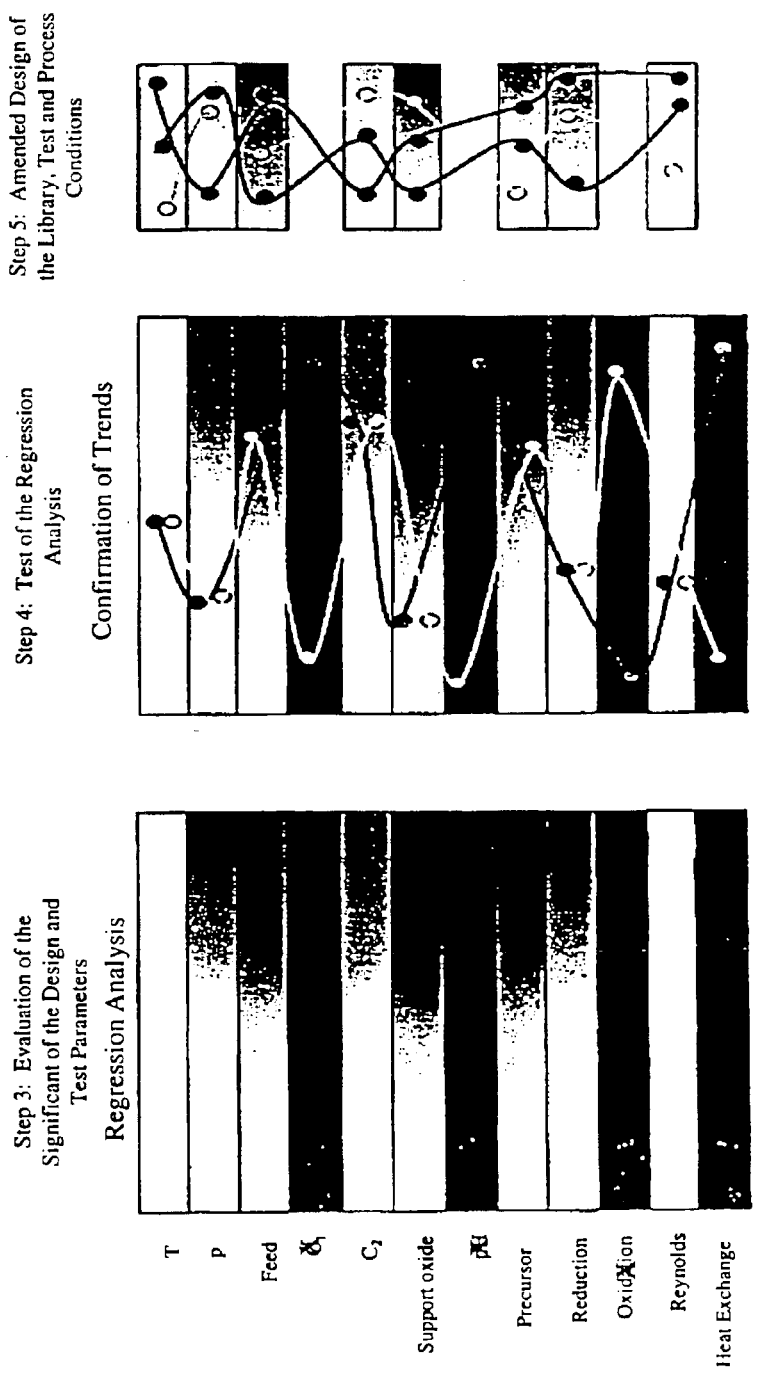
FIG. 5b shows an analysis method for restricting the parameter space.
Figure 5C:
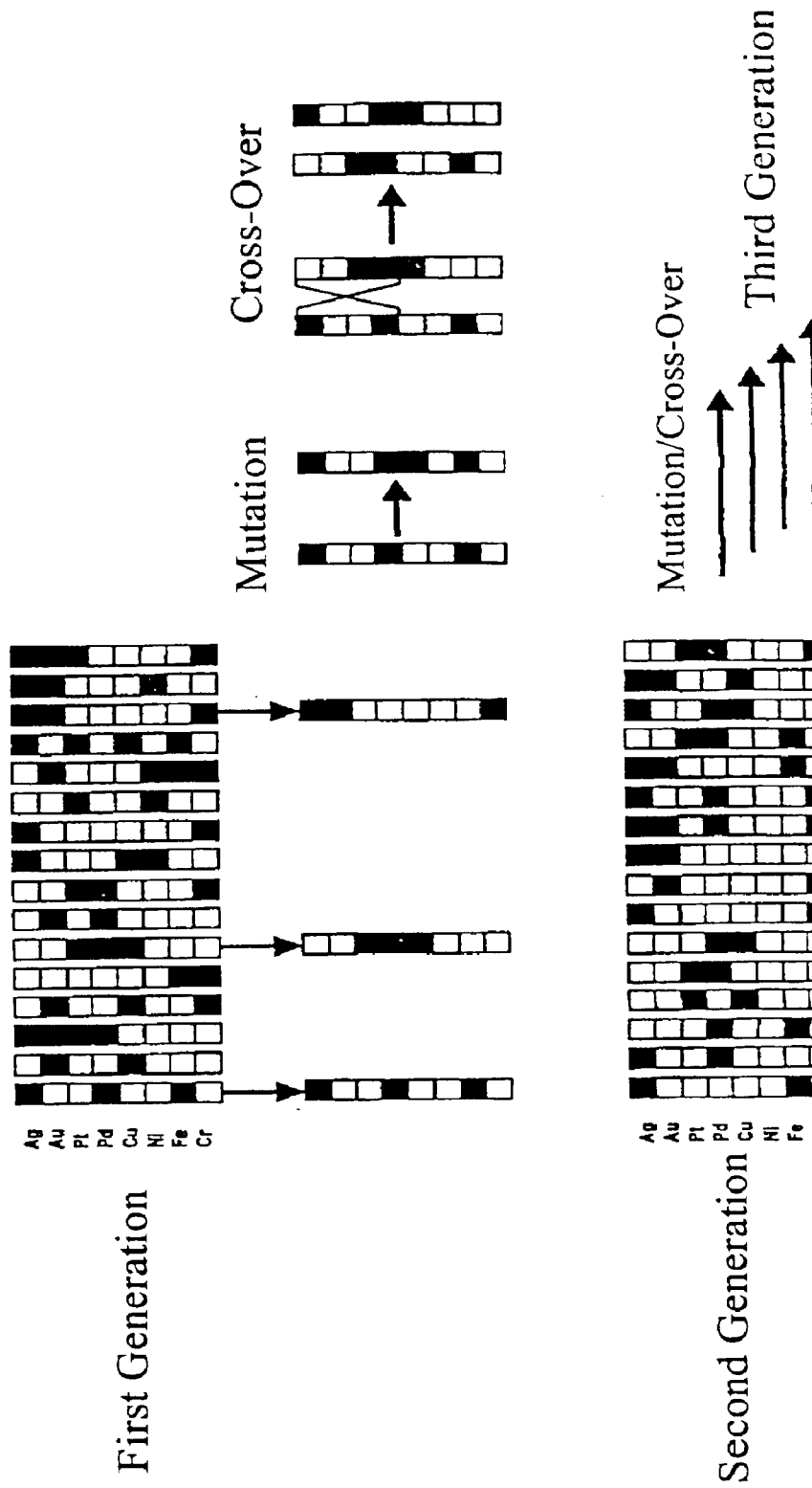
FIG. 5c shows the principle of an evolutionary algorithm.

Data analysis comprises the computer-aided evaluation of the acquired data using statistical methods. The purpose of data analysis is to look for correlations between the production parameters (characteristic properties) and the performance characteristics, to constrict the parameter spaces and thus to provide conditions for optimized substance libraries. The procedure in principle is shown in FIGS. 5a and 5b. FIG. 5c shows diagrammatically the methodology of evolutionary algorithms for preparing optimized substance libraries. In this case the production parameters of those substances which have the best performance characteristics are mutated or combined in a systematic manner, so that production parameters which have been modified in this manner are prepared for the next generation of substances.

Step 1: The production (characteristic) parameters and test parameters (each line represents the testing of a defined substance within the substance library under defined conditions) are established within a defined parameter space.

Step 2: Depending on the production parameters (characteristic parameters), for each substance there is, under defined test conditions, characterized by a complete set of test parameters, a concrete test result (for heterogeneous catalysis this is generally conversion rate and selectivity as a function of T, p, feed gas composition and the type of the reactor).

Step 3: By using statistical methods, for example classic statistical methods, regression methods, linear or non-linear regression, data mining methods, neuronal networks or evolutionary methods, for example stepwise and multiple regression, factorial regression, polynomial regression, response surface regression, principal component analysis, partial least squares, evolutionary algorithms, genetic function algorithm, the production and test parameters of the substances and if appropriate their characteristic properties are tested with respect to their effect on their performance characteristics. By this means the parameter space can be constricted and the search for optima of the target parameters can be restricted to the high-influence parameters. The choice of the preferred mathematical methods and algorithms is open in principle.

Step 4: By targeted experimenting, trends in selectivity analysis are verified.

Step 5: An optimized substance library is prepared and the cycle is run through again.

In addition, the present invention relates to a computer program having program code means for carrying out the inventive method, a data carrier containing precisely this computer program and a computer program of the type which can be carried out using the apparatus of the invention, in order to achieve implementation of the inventive method.

The present invention will now be further explained with reference to an example.

EXAMPLE

The mode of functioning of the inventive method will be explained below with reference to an example: The objective was to find the optimum production and test parameters for a complex heterogeneously catalysed reaction. The reaction selected was selective NOx reduction by hydrocarbons at Cu-containing catalysts. The catalysts were produced by automated parallel ion exchange of $\alpha\text{-Al}_2\text{O}_3$ and $\text{Al}_2\text{O}_3/\text{SiO}_2$ (zeolites) in Cu acetate. In this process 5 grams of $\alpha\text{-Al}_2\text{O}_3$ or zeolite were charged with 0.5 l of Cu acetate solution and stirred for a further 5 hours at room temperature.

The catalytic reaction took place in a 48-tube tube-bundle reactor which was operated in a fully automatic synthesis gas test plant. The reaction took place at a space velocity of 50,000 $h^{-1}$ based on the active component. The hydrocarbon (HC) used was propene. The target parameter was NOx conversion rate. The following production parameters and test parameters were varied within the specified limits:

| Parameter | Parameter type | Parameter range |
|---|---|---|
| pH during ion exchange | Production parameter | 0.68–11 |
| CuAc$_2$ concentration during ion exchange | Production parameter | 0.034–0.565 mol/l |
| Drying temperature | Production parameter | 50–200° C. |
| Calcination temperature | Production temperature | 200–700° C. |
| HC concentration | Test parameter | 4.4–2395.6 ppm |
| Temperature | Test parameter | 134.3–665.7° C. |
| Oxygen concentration | Test parameter | 1.01–8.98% by volume |

The support materials used were the following zeolite/Al$_2$O$_3$:

| | |
|---|---|
| H-ZSM-5 (module ⁻15) | ("Block 1") |
| H-ZSM-5 (module ⁻30) | ("Block 2") |
| H-ZSM-5 (module ⁻140) | ("Block 5") |
| NH4-Y (module ⁻6) | ("Block 3") |
| α-Al$_2$O$_3$ | ("Block 4") |

The orthogonal design (step 1) of the initial production and test library and the associated NOx conversion rates ("data acquisition", step 2) is shown in Table 2. The design provides the analysis of 7 parameters which are organized in five blocks (one block in each case represents the use of a zeolite or alumina) and in total 96 catalytic tests.

Figure 6:
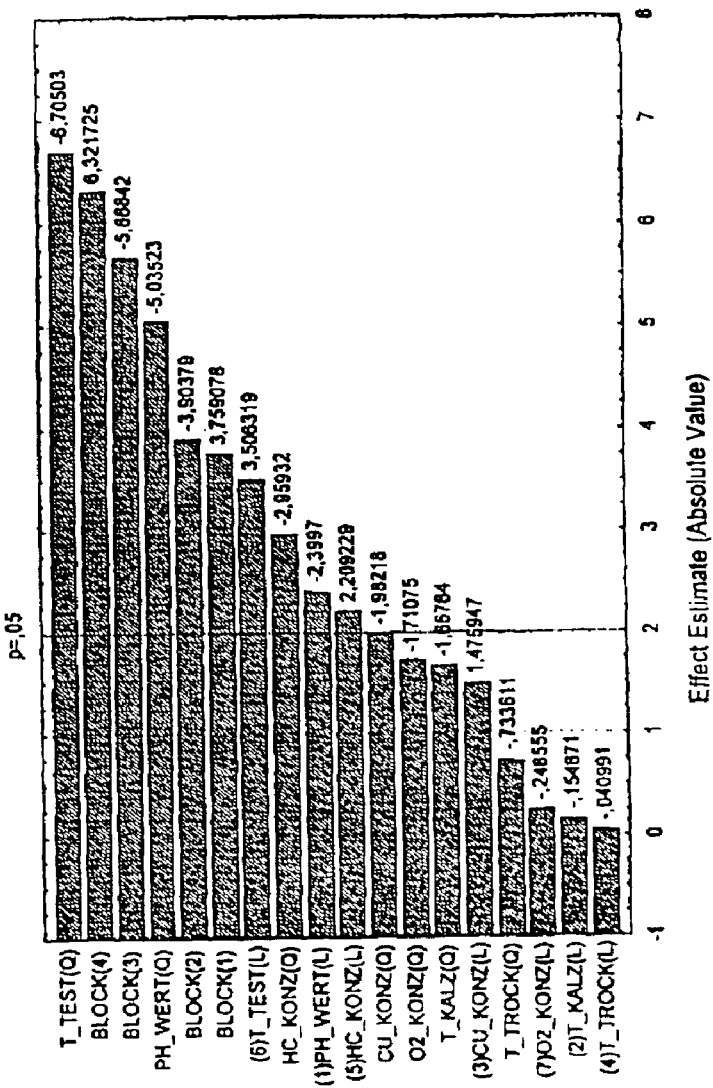
FIG. 6 summarizes the sensitivity analysis of the example of Table 2.

Using a second order regression model (step 3), the effects which the production and test parameters have on the NOx conversion rate are evaluated. FIG. 6 shows a simplified presentation of the effects in the form of a Pareto diagram. Effects which prove to be statistically relevant are (with decreasing order of effect) the test temperature, the pH during ion exchange, the HC concentration in the test gas and the CuAc$_2$ in the exchange solution. In addition, all zeolites/aluminas used differed significantly. Catalysts based on Cu-exchanged Y-zeolite or α-alumina show only low NOx activity. The parameters O$_2$ concentration, drying temperature and calcination temperature were of virtually no importance. These were kept constant in the subsequent experiments as follows:
O$_2$ concentration: 5% by volume
Drying temperature: 140° C.
Calcination temperature: 500° C.

Figure 7:
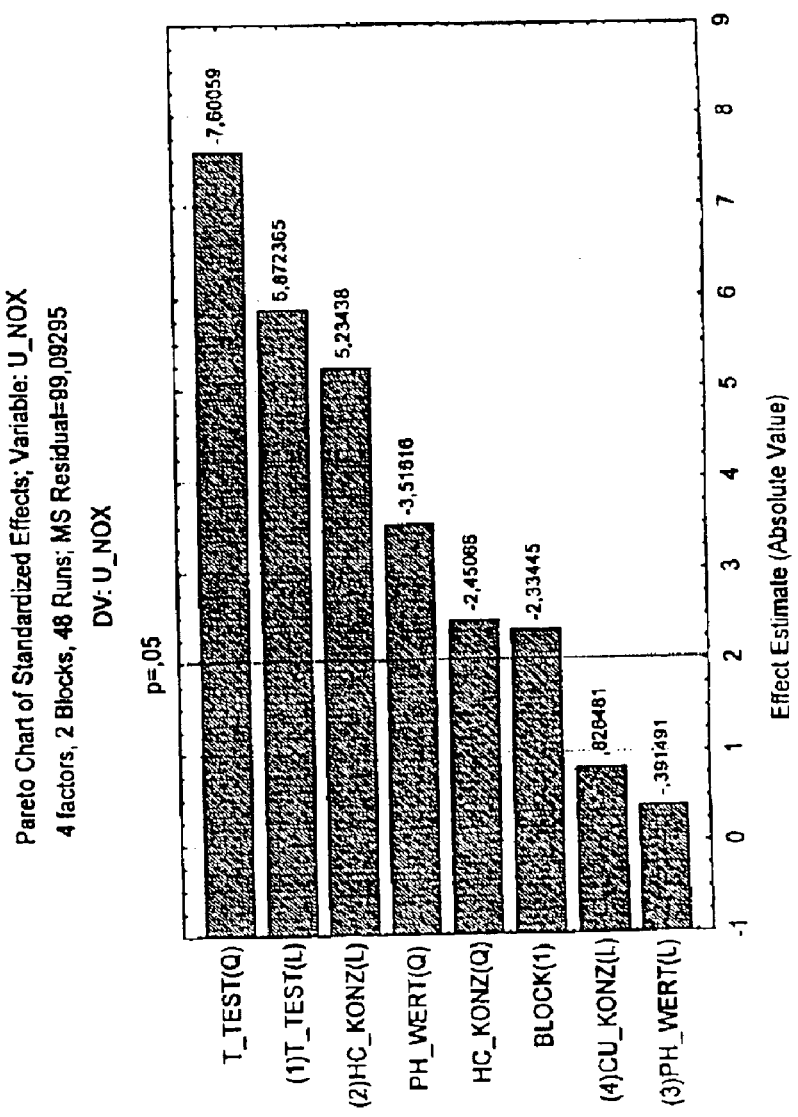
FIG. 7 shows the sensitivity analysis for the first optimized substance library from Table 3.

The subsequent 1$^{st}$ optimized substance library, which comprises in total 48 experiments, takes into account only those parameters which have proved to be significant in the initial substance library and is restricted to the two most active zeolite materials Cu/H-ZSM-5 (M⁻30) ("block 2") and Cu/H=ZSM-5 (M⁻140) ("block 5"). The design of the substance library and the associated NOx conversion rates are shown in Table 3. The decrease in the width of variation for the parameters test temperature (from 250 to 550° C.) and pH (from 4 to 8) is notable. The corresponding Pareto diagram in FIG. 7 identifies the parameters test temperature, HC concentration and pH as having particularly high effects. In addition, the data show the higher NOx activity of Cu/H-ZSM-5 (M⁻30) ("block 2") compared with Cu/H-ZSM-5 (M⁻140) ("block 5"), so that the last substance library design only takes into account the last-mentioned parameters (test temperature, HC concentration and pH) and Cu/H-ZSM-5 (M⁻30) ("block 2") (Table 4). This is composed of a further 16 experiments (25 to 40), together with 24 experiments (1 to 24) which were carried out in the preceding substance library on Cu/H-ZSM-5 (M⁻30) ("block 2"). The CuAc$_2$ concentration was kept constant for the new 16 experiments at 0.3 mol/l.

Using a simplex algorithm, the NOx conversion rate maximum was found at the following parameter setting: T=418° C., HC concentration=1698 ppm, pH for the Cu ion exchange: 6.1.

Moreover, the mathematical models mentioned above under "step 3" are fundamentally suitable for analyzing a substance library:

The discovery of extreme values within a parameter space can be carried out using the customary methods, for example the simplex method, the method of Powell, Quasi-Newton methods, or the method of "simulated annealing".

TABLE 1

1. Production parameters of the most important preparation methods for cataylsts

| 1. Precipitation/ coprecipitation | 2. (Metal) adsorption to support | 3. Pore filling/ incipient wetness |
|---|---|---|
| Precursor | Precursor (interaction with the support) | Precursor |
| Support characteristics | Support characteristics | |
| Temperature (temperature program etc.) | Support characteristics Temperature (temperature program etc.) | Agitation/mixing Concentrations Viscosity of the precursor solution |
| Precipitation reagents (C$_2$O$_4{}^{2-}$, CO$_3{}^{2-}$, OH-urea etc.) | Injection rate, agitation pH | Pressure Drying (static/flowing gas atmosphere) |
| Injection rate, agitation pH Concentration | Concentrations Viscosity of the precursor solution | Calcination (reducing/ oxidizing atmosphere, temperature rise, |
| Ageing of the suspensions (time, temperature) | Washing (pH, salts, temperature, volume, agitation) | maximum temperature) |
| Washing (pH, salts, temperature, volume, agitation) | Drying (static/flowing gas atmosphere) Calcination (reducing/ | |
| Drying (static/flowing gas atmosphere) | oxidizing atmosphere, temperature rise, | |
| Calcination (reducing/ oxidizing atmosphere, temperature rise, maximum temperature) | maximum temperature) | |

TABLE 2

2. Production parameters, test parameters and measured NOx conversion rate of the initial library, test 1 - 48

|    | BLOCK | PH     | T_CALC  | CU_CONC | T_DRY   | HC_CONC  | T_TEST  | O2_CONC | U_NOX  |
|----|-------|--------|---------|---------|---------|----------|---------|---------|--------|
| 1  | 1     | 4.000  | 400.000 | .200    | 80.000  | 1650.000 | 300.000 | 3.500   | 7.000  |
| 2  | 1     | 4.000  | 400.000 | .200    | 160.000 | 750.000  | 500.000 | 6.500   | 25.000 |
| 3  | 1     | 4.000  | 400.000 | .400    | 80.000  | 1650.000 | 300.000 | 6.500   | 10.000 |
| 4  | 1     | 4.000  | 400.000 | .400    | 160.000 | 750.000  | 500.000 | 3.500   | 28.000 |
| 5  | 1     | 4.000  | 600.000 | .200    | 80.000  | 1650.000 | 500.000 | 3.500   | 28.000 |
| 6  | 1     | 4.000  | 600.000 | .200    | 160.000 | 750.000  | 300.000 | 6.500   | 4.000  |
| 7  | 1     | 4.000  | 600.000 | .400    | 80.000  | 1650.000 | 500.000 | 6.500   | 32.000 |
| 8  | 1     | 4.000  | 600.000 | .400    | 160.000 | 750.000  | 300.000 | 3.500   | 9.000  |
| 9  | 1     | 8.000  | 400.000 | .200    | 80.000  | 750.000  | 300.000 | 3.500   | 4.000  |
| 10 | 1     | 8.000  | 400.000 | .200    | 160.000 | 1650.000 | 500.000 | 6.500   | 16.000 |
| 11 | 1     | 8.000  | 400.000 | .400    | 80.000  | 750.000  | 300.000 | 6.500   | 2.000  |
| 12 | 1     | 8.000  | 400.000 | .400    | 160.000 | 1650.000 | 500.000 | 3.500   | 14.000 |
| 13 | 1     | 8.000  | 600.000 | .200    | 80.000  | 750.000  | 500.000 | 3.500   | 8.000  |
| 14 | 1     | 8.000  | 600.000 | .200    | 160.000 | 1650.000 | 300.000 | 6.500   | 4.000  |
| 15 | 1     | 8.000  | 600.000 | .400    | 80.000  | 750.000  | 500.000 | 6.500   | 11.000 |
| 16 | 1     | 8.000  | 600.000 | .400    | 160.000 | 1650.000 | 300.000 | 3.500   | 8.000  |
| 17 | 1     | 6.000  | 500.000 | .300    | 120.000 | 1200.000 | 400.000 | 5.000   | 68.000 |
| 18 | 2     | 4.000  | 400.000 | .200    | 80.000  | 750.000  | 500.000 | 3.500   | 36.000 |
| 19 | 2     | 4.000  | 400.000 | .200    | 160.000 | 1650.000 | 300.000 | 6.500   | 15.000 |
| 20 | 2     | 4.000  | 400.000 | .400    | 80.000  | 750.000  | 500.000 | 6.500   | 40.000 |
| 21 | 2     | 4.000  | 400.000 | .400    | 160.000 | 1650.000 | 300.000 | 3.500   | 18.000 |
| 22 | 2     | 4.000  | 600.000 | .200    | 80.000  | 750.000  | 300.000 | 3.500   | 15.000 |
| 23 | 2     | 4.000  | 600.000 | .200    | 160.000 | 1650.000 | 500.000 | 6.500   | 36.000 |
| 24 | 2     | 4.000  | 600.000 | .400    | 80.000  | 750.000  | 300.000 | 6.500   | 15.000 |
| 25 | 2     | 4.000  | 600.000 | .400    | 160.000 | 1650.000 | 500.000 | 3.500   | 39.000 |
| 26 | 2     | 8.000  | 400.000 | .200    | 80.000  | 1650.000 | 500.000 | 3.500   | 23.000 |
| 27 | 2     | 8.000  | 400.000 | .200    | 160.000 | 750.000  | 300.000 | 6.500   | 6.000  |
| 28 | 2     | 8.000  | 400.000 | .400    | 80.000  | 1650.000 | 500.000 | 6.500   | 27.000 |
| 29 | 2     | 8.000  | 400.000 | .400    | 160.000 | 750.000  | 300.000 | 3.500   | 12.000 |
| 30 | 2     | 8.000  | 600.000 | .200    | 80.000  | 1650.000 | 300.000 | 3.500   | 9.000  |
| 31 | 2     | 8.000  | 600.000 | .200    | 160.000 | 750.000  | 500.000 | 6.500   | 15.000 |
| 32 | 2     | 8.000  | 600.000 | .400    | 80.000  | 1650.000 | 300.000 | 6.500   | 11.000 |
| 33 | 2     | 8.000  | 600.000 | .400    | 160.000 | 750.000  | 500.000 | 3.500   | 17.000 |
| 34 | 2     | 6.000  | 500.000 | .300    | 120.000 | 1200.000 | 400.000 | 5.000   | 79.000 |
| 35 | 3     | 4.000  | 400.000 | .200    | 80.000  | 750.000  | 300.000 | 6.500   | 2.000  |
| 36 | 3     | 4.000  | 400.000 | .200    | 160.000 | 1650.000 | 500.000 | 3.500   | 7.000  |
| 37 | 3     | 4.000  | 400.000 | .400    | 80.000  | 750.000  | 300.000 | 3.500   | 5.000  |
| 38 | 3     | 4.000  | 400.000 | .400    | 160.000 | 1650.000 | 500.000 | 6.500   | 8.000  |
| 39 | 3     | 4.000  | 600.000 | .200    | 80.000  | 750.000  | 500.000 | 6.500   | 6.000  |
| 40 | 3     | 4.000  | 600.000 | .200    | 160.000 | 1650.000 | 300.000 | 3.500   | 4.000  |
| 41 | 3     | 4.000  | 600.000 | .400    | 80.000  | 750.000  | 500.000 | 3.500   | 5.000  |
| 42 | 3     | 4.000  | 600.000 | .400    | 160.000 | 1650.000 | 300.000 | 6.500   | 4.000  |
| 43 | 3     | 8.000  | 400.000 | .200    | 80.000  | 1650.000 | 300.000 | 6.500   | 2.000  |
| 44 | 3     | 8.000  | 400.000 | .200    | 160.000 | 750.000  | 500.000 | 3.500   | 5.000  |
| 45 | 3     | 8.000  | 400.000 | .400    | 80.000  | 1650.000 | 300.000 | 3.500   | 4.000  |
| 46 | 3     | 8.000  | 400.000 | .400    | 160.000 | 750.000  | 500.000 | 6.500   | 4.000  |
| 47 | 3     | 8.000  | 600.000 | .200    | 80.000  | 1650.000 | 500.000 | 6.500   | 8.000  |
| 48 | 3     | 8.000  | 600.000 | .200    | 160.000 | 750.000  | 300.000 | 3.500   | 6.000  |
| 49 | 3     | 8.000  | 600.000 | .400    | 80.000  | 1650.000 | 500.000 | 3.500   | 9.000  |
| 50 | 3     | 8.000  | 600.000 | .400    | 160.000 | 750.000  | 500.000 | 6.500   | 5.000  |
| 51 | 3     | 6.000  | 500.000 | .300    | 120.000 | 1200.000 | 400.000 | 5.000   | 12.000 |
| 52 | 4     | 4.000  | 400.000 | .200    | 80.000  | 1650.000 | 500.000 | 6.500   | 1.000  |
| 53 | 4     | 4.000  | 400.000 | .200    | 160.000 | 750.000  | 300.000 | 3.500   | 2.000  |
| 54 | 4     | 4.000  | 400.000 | .400    | 80.000  | 1650.000 | 500.000 | 3.500   | 1.000  |
| 55 | 4     | 4.000  | 400.000 | .400    | 160.000 | 750.000  | 300.000 | 6.500   | 0.000  |
| 56 | 4     | 4.000  | 600.000 | .200    | 80.000  | 1650.000 | 300.000 | 6.500   | 2.000  |
| 57 | 4     | 4.000  | 600.000 | .200    | 160.000 | 750.000  | 300.000 | 3.500   | 3.000  |
| 58 | 4     | 4.000  | 600.000 | .400    | 80.000  | 1650.000 | 300.000 | 3.500   | 8.000  |
| 59 | 4     | 4.000  | 600.000 | .400    | 160.000 | 750.000  | 500.000 | 6.500   | 2.000  |
| 60 | 4     | 8.000  | 400.000 | .200    | 80.000  | 750.000  | 500.000 | 6.500   | 1.000  |
| 61 | 4     | 8.000  | 400.000 | .200    | 160.000 | 1650.000 | 300.000 | 3.500   | 2.000  |
| 62 | 4     | 8.000  | 400.000 | .400    | 80.000  | 750.000  | 500.000 | 3.500   | 1.000  |
| 63 | 4     | 8.000  | 400.000 | .400    | 160.000 | 1650.000 | 300.000 | 6.500   | 2.000  |
| 64 | 4     | 8.000  | 600.000 | .200    | 80.000  | 750.000  | 300.000 | 6.500   | 1.000  |
| 65 | 4     | 8.000  | 600.000 | .200    | 160.000 | 1650.000 | 500.000 | 3.500   | 2.000  |
| 66 | 4     | 8.000  | 600.000 | .400    | 80.000  | 750.000  | 300.000 | 3.500   | 2.000  |
| 67 | 4     | 8.000  | 600.000 | .400    | 160.000 | 1650.000 | 500.000 | 6.500   | 1.000  |
| 68 | 4     | 6.000  | 500.000 | .300    | 120.000 | 1200.000 | 400.000 | 5.000   | 1.000  |
| 69 | 9     | .686   | 500.000 | .300    | 120.000 | 1200.000 | 400.000 | 5.000   | 24.000 |
| 70 | 5     | 11.314 | 500.000 | .300    | 120.000 | 1200.000 | 400.000 | 5.000   | 11.000 |
| 71 | 5     | 6.000  | 234.316 | .300    | 120.000 | 1200.000 | 400.000 | 5.000   | 50.000 |
| 72 | 5     | 6.000  | 765.684 | .300    | 120.000 | 1200.000 | 400.000 | 5.000   | 45.000 |
| 73 | 5     | 6.000  | 500.000 | .034    | 120.000 | 1200.000 | 400.000 | 5.000   | 31.000 |
| 74 | 5     | 6.000  | 500.000 | .566    | 120.000 | 1200.000 | 400.000 | 5.000   | 60.000 |

TABLE 2-continued

2. Production parameters, test parameters and measured NOx conversion rate of the initial library, test 1 - 48

| | BLOCK | PH | T_CALC | CU_CONC | T_DRY | HC_CONC | T_TEST | O2_CONC | U_NOX |
|---|---|---|---|---|---|---|---|---|---|
| 75 | 5 | 6.000 | 500.000 | .300 | 13.726 | 1200.000 | 400.000 | 5.000 | 56.000 |
| 76 | 5 | 6.000 | 500.000 | .300 | 226.274 | 1200.000 | 400.000 | 5.000 | 58.000 |
| 77 | 5 | 6.000 | 500.000 | .300 | 120.000 | 4.420 | 400.000 | 5.000 | 2.000 |
| 78 | 5 | 6.000 | 500.000 | .300 | 120.000 | 2395.580 | 400.000 | 5.000 | 71.000 |
| 79 | 5 | 6.000 | 500.000 | .300 | 120.000 | 1200.000 | 134.316 | 5.000 | 0.000 |
| 80 | 5 | 6.000 | 500.000 | .300 | 120.000 | 1200.000 | 665.684 | 5.000 | 4.000 |
| 81 | 5 | 6.000 | 500.000 | .300 | 120.000 | 1200.000 | 400.000 | 1.015 | 48.000 |
| 82 | 5 | 6.000 | 500.000 | .300 | 120.000 | 1200.000 | 400.000 | 8.985 | 48.000 |
| 83 | 5 | 4.000 | 400.000 | .300 | 120.000 | 1200.000 | 400.000 | 5.000 | 36.000 |
| 84 | 5 | 4.000 | 400.000 | .200 | 80.000 | 750.000 | 500.000 | 3.500 | 26.000 |
| 85 | 5 | 4.000 | 400.000 | .200 | 160.000 | 1650.000 | 300.000 | 6.500 | 12.000 |
| 86 | 5 | 4.000 | 400.000 | .400 | 80.000 | 750.000 | 500.000 | 6.500 | 31.000 |
| 87 | 5 | 4.000 | 600.000 | .400 | 160.000 | 1650.000 | 300.000 | 3.500 | 14.000 |
| 88 | 5 | 4.000 | 600.000 | .200 | 80.000 | 750.000 | 300.000 | 3.500 | 11.000 |
| 89 | 5 | 4.000 | 600.000 | .200 | 160.000 | 1650.000 | 500.000 | 6.500 | 29.000 |
| 90 | 5 | 8.000 | 400.000 | .400 | 80.000 | 1650.000 | 500.000 | 6.500 | 19.000 |
| 91 | 5 | 8.000 | 400.000 | .200 | 160.000 | 750.000 | 300.000 | 3.500 | 4.000 |
| 92 | 5 | 8.000 | 400.000 | .200 | 80.000 | 1650.000 | 500.000 | 6.500 | 22.000 |
| 93 | 5 | 8.000 | 400.000 | .400 | 160.000 | 750.000 | 300.000 | 3.500 | 9.000 |
| 94 | 5 | 8.000 | 600.000 | .400 | 80.000 | 1650.000 | 300.000 | 6.500 | 6.000 |
| 95 | 5 | 8.000 | 600.000 | .200 | 160.000 | 750.000 | 500.000 | 3.500 | 13.000 |
| 96 | 5 | 8.000 | 600.000 | .200 | 80.000 | 1650.000 | 300.000 | 6.500 | 7.000 |

TABLE 3

3. Production parameters, test parameters and measured NOx conversion rate of the 1st optimised library, parameter space was constricted and the variable range reduced

| | BLOCK | T_TEST | HC_CONC | PH | CU_CONC | U_NOX |
|---|---|---|---|---|---|---|
| 1 | 2 | 325.000 | 750.000 | 5.000 | .200 | 17.000 |
| 2 | 2 | 325.000 | 750.000 | 5.000 | .400 | 21.000 |
| 3 | 2 | 325.000 | 750.000 | 7.000 | .200 | 13.000 |
| 4 | 2 | 325.000 | 750.000 | 7.000 | .400 | 17.000 |
| 5 | 2 | 325.000 | 1650.000 | 5.000 | .200 | 26.000 |
| 6 | 2 | 325.000 | 1650.000 | 5.000 | .400 | 31.000 |
| 7 | 2 | 325.000 | 1650.000 | 7.000 | .200 | 19.000 |
| 8 | 2 | 325.000 | 1650.000 | 7.000 | .400 | 24.000 |
| 9 | 2 | 475.000 | 750.000 | 5.000 | .200 | 43.000 |
| 10 | 2 | 475.000 | 750.000 | 5.000 | .400 | 45.000 |
| 11 | 2 | 475.000 | 750.000 | 7.000 | .200 | 41.000 |
| 12 | 2 | 475.000 | 750.000 | 7.000 | .400 | 38.000 |
| 13 | 2 | 475.000 | 1650.000 | 5.000 | .200 | 51.000 |
| 14 | 2 | 475.000 | 1650.000 | 5.000 | .400 | 52.000 |
| 15 | 2 | 475.000 | 1650.000 | 7.000 | .200 | 48.000 |
| 16 | 2 | 475.000 | 1650.000 | 7.000 | .400 | 49.000 |
| 17 | 2 | 250.000 | 1200.000 | 6.000 | .300 | 7.000 |
| 18 | 2 | 550.000 | 1200.000 | 6.000 | .300 | 16.000 |
| 19 | 2 | 400.000 | 300.000 | 6.000 | .300 | 21.000 |
| 20 | 2 | 400.000 | 2100.000 | 6.000 | .300 | 85.000 |
| 21 | 2 | 400.000 | 1200.000 | 4.000 | .300 | 35.000 |
| 22 | 2 | 400.000 | 1200.000 | 8.000 | .300 | 52.000 |
| 23 | 2 | 400.000 | 1200.000 | 6.000 | .100 | 71.000 |
| 24 | 2 | 400.000 | 1200.000 | 6.000 | .500 | 74.000 |
| 25 | 5 | 325.000 | 750.000 | 5.000 | .200 | 13.000 |
| 26 | 5 | 325.000 | 750.000 | 5.000 | .400 | 19.000 |
| 27 | 5 | 325.000 | 750.000 | 7.000 | .200 | 10.000 |
| 28 | 5 | 325.000 | 750.000 | 7.000 | .400 | 12.000 |
| 29 | 5 | 325.000 | 1650.000 | 5.000 | .200 | 22.000 |
| 30 | 5 | 325.000 | 1650.000 | 5.000 | .400 | 26.000 |
| 31 | 5 | 325.000 | 1650.000 | 7.000 | .200 | 14.000 |
| 32 | 5 | 325.000 | 1650.000 | 7.000 | .400 | 20.000 |
| 33 | 5 | 475.000 | 750.000 | 5.000 | .200 | 36.000 |
| 34 | 5 | 475.000 | 750.000 | 5.000 | .400 | 38.000 |
| 35 | 5 | 475.000 | 750.000 | 7.000 | .200 | 32.000 |
| 36 | 5 | 475.000 | 750.000 | 7.000 | .400 | 30.000 |
| 37 | 5 | 475.000 | 1650.000 | 5.000 | .200 | 46.000 |
| 38 | 5 | 475.000 | 1650.000 | 5.000 | .400 | 45.000 |
| 39 | 5 | 475.000 | 1650.000 | 7.000 | .200 | 41.000 |
| 40 | 5 | 475.000 | 1650.000 | 7.000 | .400 | 42.000 |
| 41 | 5 | 250.000 | 1200.000 | 6.000 | .300 | 7.000 |
| 42 | 5 | 550.000 | 1200.000 | 6.000 | .300 | 14.000 |
| 43 | 5 | 400.000 | 300.000 | 6.000 | .300 | 16.000 |
| 44 | 5 | 400.000 | 2100.000 | 6.000 | .300 | 67.000 |
| 45 | 5 | 400.000 | 1200.000 | 4.000 | .300 | 31.000 |
| 46 | 5 | 400.000 | 1200.000 | 8.000 | .300 | 41.000 |
| 47 | 5 | 400.000 | 1200.000 | 6.000 | .100 | 53.000 |
| 48 | 5 | 400.000 | 1200.000 | 6.000 | .500 | 60.000 |

TABLE 4

4. Production parameters, test parameters and measured NOx conversion rate of the 2nd optimized library, parameter space was further constricted and the variable range reduced, optimum (saddle point) determined via the simplex method

| | T_TEST | HC_CONC | PH | U_NOX |
|---|---|---|---|---|
| 1 | 325.000 | 750.000 | 5.000 | 17.000 |
| 2 | 325.000 | 750.000 | 5.000 | 21.000 |
| 3 | 325.000 | 750.000 | 7.000 | 13.000 |
| 4 | 325.000 | 750.000 | 7.000 | 17.000 |
| 5 | 325.000 | 1650.000 | 5.000 | 26.000 |
| 6 | 325.000 | 1650.000 | 5.000 | 31.000 |
| 7 | 325.000 | 1650.000 | 7.000 | 19.000 |
| 8 | 325.000 | 1650.000 | 7.000 | 24.000 |
| 9 | 475.000 | 750.000 | 5.000 | 43.000 |
| 10 | 475.000 | 750.000 | 5.000 | 45.000 |
| 11 | 475.000 | 750.000 | 7.000 | 41.000 |
| 12 | 475.000 | 750.000 | 7.000 | 38.000 |
| 13 | 475.000 | 1650.000 | 5.000 | 51.000 |
| 14 | 475.000 | 1650.000 | 5.000 | 52.000 |
| 15 | 475.000 | 1650.000 | 7.000 | 48.000 |
| 16 | 475.000 | 1650.000 | 7.000 | 49.000 |
| 17 | 250.000 | 1200.000 | 6.000 | 7.000 |
| 18 | 550.000 | 1200.000 | 6.000 | 16.000 |

TABLE 4-continued

4. Production parameters, test parameters and measured NOx conversion rate of the 2$^{nd}$ optimized library, parameter space was further constricted and the variable range reduced, optimum (saddle point) determined via the simplex method

|    | T_TEST  | HC_CONC  | PH    | U_NOX  |
|----|---------|----------|-------|--------|
| 19 | 400.000 | 300.000  | 6.000 | 21.000 |
| 20 | 400.000 | 2100.000 | 6000  | 85.000 |
| 21 | 400.000 | 1200.000 | 4.000 | 35.000 |
| 22 | 400.000 | 1200.000 | 8.000 | 32.000 |
| 23 | 400.000 | 1200.000 | 6.000 | 71.000 |
| 24 | 400.000 | 1200.000 | 6.000 | 74.000 |
| 25 | 375.000 | 750.000  | 5.500 | 48.000 |
| 26 | 375.000 | 1650.000 | 5.500 | 64.000 |
| 27 | 375.000 | 750.000  | 6.800 | 76.000 |
| 28 | 375.000 | 1650.000 | 6.800 | 84.000 |
| 29 | 425.000 | 750.000  | 5.500 | 61.000 |
| 30 | 425.000 | 1650.000 | 5.500 | 68.000 |
| 31 | 425.000 | 750.000  | 6.800 | 67.000 |
| 32 | 425.000 | 1650.000 | 6.800 | 81.000 |
| 33 | 357.955 | 1200.000 | 6.150 | 55.000 |
| 34 | 442.045 | 1200.000 | 6.150 | 51.000 |
| 35 | 400.000 | 1200.000 | 5.057 | 41.000 |
| 36 | 400.000 | 1200.000 | 7.243 | 59.000 |
| 37 | 400.000 | 443.193  | 6.150 | 34.000 |
| 38 | 400.000 | 1956.807 | 6.150 | 88.000 |
| 39 | 400.000 | 1200.000 | 6.150 | 73.000 |
| 40 | 400.000 | 1200.000 | 6.150 | 73.000 |

Optimum:
T: 418° C.
pH: 6.1
HC concentration: 1698 ppm

The present invention is by no intent limited to the embodiment described heretofore, and modification may be made without departing from invention.

German priority application No. 10028875.8, filed Jun. 10, 2000, including the specification, drawings, claims and abstract, is hereby incorporated by reference.

What is claimed is:

1. A method for the automated production and iterative automated optimization of a substance library having at least two substances or at least one reaction parameter relating to a performance characteristic of the substance library, the method comprising the steps of:
   (a) defining at least one production parameter and at least one test parameter;
   (b) automated preparation of the substance library by producing at least two substances on the basis of the at least one production parameter;
   (c) automated testing of the at least two substances of the substance library with respect to at least one performance characteristic on the basis of the at least one test parameter;
   (d) evaluating the test using electronic data analysis; and
   (e) varying the at least one production parameter and/or the at least one test parameter for optimizing the performance characteristics, to perform single or repeated iterations of steps b) to e) or c) to e),
   wherein the steps b) to e) are carried out as an integrated automated process.

2. The method according to claim 1, wherein the results of the tests in step c) are stored in a database together with the associated at least one production parameter and/or test parameter.

3. The method according to claim 2, wherein the results are stored using a system time, the system location of at least one substance library and/or the substance identification as assignment criterion.

4. The method according to claim 1, wherein one or more effects of individual production parameters and test parameters on performance characteristics is determined by data analysis.

5. The method according to claim 2, wherein one or more effects of individual production parameters and test parameters on performance characteristics is determined by data analysis.

6. The method according to claim 3, wherein one or more effects of individual production parameters and test parameters on performance characteristics is determined by data analysis.

7. The method according to claim 1, wherein the data analysis comprises using classical statistical methods, regression methods, linear or nonlinear regression, data mining methods, neural networks or evolutionary methods.

8. The method according to claim 4, wherein parameters determined by data analysis as having a negligible effect on the performance characteristics are either kept constant or are not considered in subsequent iterations in step d).

9. The method according to claim 7, wherein parameters determined by data analysis as having a negligible effect on the performance characteristics are either kept constant in subsequent iterations or are not considered in step d).

10. The method according to claim 1, wherein the at least two substances comprise either molecular substances, non-molecular substances, formulations, materials, or mixtures of two or more thereof.

11. The method according to claim 10, wherein the at least two substances of the substance library are selected from the group consisting of heterogeneous or heterogenized catalysts, luminophores, electrooptical, superconducting or magnetic substances, or mixtures of two or more thereof.

12. The method according to claim 10, wherein the at least two substances of the substance library are selected from the group consistent of intermetallic compounds, oxides, oxide mixtures, mixed oxides, ionic or covalent compounds of metals and/or nonmetals, metal alloys, ceramics, organometallic compounds and composite materials, dielectrics, thermoelectrics, magnetoresistive and magnetooptical materials, organic compounds, enzymes, active pharmaceutical compounds, substances for foodstuffs and food supplements, feedstuffs and feed supplements and cosmetics and mixtures of two or more thereof.

13. The method according to claim 10, wherein the performance characteristics comprise activity and selectivity in one or more chemical reactions catalysed by at least one catalyst.

14. The method according to claim 11, wherein the performance characteristics comprise activity and selectivity in one or more chemical reactions catalysed by at least one catalyst.

15. The method according to claim 11, wherein the test parameters comprise reactor type, operating temperature of at least one catalyst and/or of starting material fluid and pressure and/or composition of the starting material fluid and/or residence time and/or space velocity.

16. The method according to claim 13 wherein the test parameters comprise reactor type, operating temperature of the at least one catalyst and/or of starting material fluid and pressure and/or composition of the starting material fluid and/or residence time and/or space velocity.

17. The method according to claim 14, wherein the test parameters comprise reactor type, operating temperature of at least one catalyst and/or of starting material fluid and pressure and/or composition of the starting material fluid and/or residence time and/or space velocity.

18. The method according to claim 1, wherein the substance library is either arranged linearly or in a multidimensional matrix.

19. An apparatus for the automated production and iterative automated optimization of a substance library, comprising:
- defining means for defining at least one initial production parameter and at least one test parameter;
- preparation means for automated preparation of a substance library including automated producing of at least two substances of the substance library on the basis of the at least one production parameter;
- a test device that tests the at least two substances of the substance library with respect to at least one performance characteristic on the basis of the at least one test parameter;
- a data analysis system for evaluating the tests;
- a device for varying the at least one production parameter and/or test parameter for optimising the performance characteristics, and
- control means for integrated and automated control of the defining means, the preparation means, the test device, the data analysis system, and the device.

20. The apparatus according to claim 19 further comprising storage means for storing test results in a database associated with at least one production parameter and/or test parameter and/or system time or absolute position of the tested substance.

21. Substrate comprising at least one substance library comprising at least two substances, wherein the substance library is obtainable by a method for the automated production and iterative automated optimization of a substance library and/or at least one reaction parameter, the method comprising the steps:
(a) defining at least one production parameter and at least one test parameter;
(b) automated preparation of a substance library by producing at least two substances on the basis of the at least one production parameter;
(c) automated testing of the at least two substances of the substance library with respect to at least one desired useful property on the basis of the at least one test parameter;
(d) evaluating the test using electronic data analysis; and
(e) varying the at least one production parameter and/or the at least one test parameter for optimizing the desired useful properties, to perform single or repeated iterations of steps b) to e) or c) to e),
wherein the steps b) to e) are carried out as an integrated automated process.

22. A computer readable data storage medium having computer program code recorded thereon executable by a computer, the computer program code comprising:
- a first program code for defining at least one production parameter and at least one test parameter;
- a second program code for automated preparation of a substance library by producing at least two substances on the basis of the at least one production parameter;
- a third program code for automated testing of the at least two substances of the substance library with respect to at least one performance characteristic on the basis of the at least one test parameter;
- a fourth program code that evaluates the test using data analysis;
- a fifth program code that varies the at least one production parameter and/or the at least one test parameter for optimizing the test characteristics and to perform single or repeated iterations of the first to fourth program codes; and
- a control program code that controls execution of the first to fifth program codes as an automated and integrated process.

23. The computer readable data storage medium according to claim 22, further comprising:
a sixth program code that stores results of the automated testing in a database associated with at least one production parameter and/or test parameter.

24. The computer readable data storage medium according to claim 22, wherein the fourth program code evaluated effects of individual production parameters and test parameters on performance characteristics.

25. The computer readable data storage medium according to claim 22, wherein the data analysis comprises classical statistical methods, regression methods, linear or nonlinear regression, data mining methods, neural networks, or evolutionary methods.

26. The computer readable data storage medium according to claim 22, wherein parameters determined by the fourth program code as having a negligible effect on the performance characteristics is either kept constant or not considered in subsequent iterations by the fifth program code.

27. The computer readable data storage medium according to claim 22, wherein the at least two substances comprise either molecular substances, non-molecular substances, formulations, materials, or mixtures of two or more thereof.

28. The computer readable data storage medium according to claim 22, wherein the at least two substances of the substance library are selected from heterogeneous or heterogenized catalysts, luminophores, electrooptical, superconducting or magnetic substances, or mixtures of two or more thereof.

29. The computer readable data storage medium according to claim 22, wherein the at least two substances of the substance library are selected from intermetallic compounds, oxides, oxide mixtures, mixed oxides, ionic or covalent compounds of metals and/or nonmetals, metal alloys, ceramics, organometallic compounds and composite materials, dielectrics, thermoelectrics, magnetoresistive and magnetooptical materials, organic compounds, enzymes, active pharmaceutical compounds, substances for foodstuffs and food supplements, feedstuffs and feed supplements and cosmetics and mixtures of two or more thereof.

30. The computer readable data storage medium according to claim 22, wherein the performance characteristics comprise activity and selectivity in one or more chemical reactions catalysed by at least one catalyst.

31. The computer readable data storage medium according to claim 22, wherein the test parameters comprise reactor type, operating temperature of the at least one catalyst and/or of the starting material fluid and the pressure and/or the composition of the starting material fluid and/or residence time and/or space velocity.

32. The computer readable data storage medium according to claim 22, wherein the substance library is either arranged linearly or in a multidimensional matrix.

* * * * *